(12) United States Patent
Blomqvist

(10) Patent No.: US 8,321,015 B2
(45) Date of Patent: Nov. 27, 2012

(54) METHOD AND IMPLANTABLE DEVICE FOR SELECTIVE HEART PACING

(75) Inventor: Andreas Blomqvist, Spånga (SE)

(73) Assignee: St. Jude Medical AB, Jarfalla (SE)

( * ) Notice: Subject to any disclaimer, the term of this patent is extended or adjusted under 35 U.S.C. 154(b) by 52 days.

(21) Appl. No.: 13/119,992

(22) PCT Filed: Sep. 23, 2008

(86) PCT No.: PCT/SE2008/000523
§ 371 (c)(1),
(2), (4) Date: Mar. 21, 2011

(87) PCT Pub. No.: WO2010/036151
PCT Pub. Date: Apr. 1, 2010

(65) Prior Publication Data
US 2011/0202102 A1    Aug. 18, 2011

(51) Int. Cl.
*A61N 1/00* (2006.01)
(52) U.S. Cl. .......................................................... 607/11
(58) Field of Classification Search .................. 607/11, 607/9, 17
See application file for complete search history.

(56) References Cited

U.S. PATENT DOCUMENTS

| 5,891,176 A | 4/1999 | Bornzin |
| 6,763,267 B2 | 7/2004 | Ding |
| 2003/0060851 A1 | 3/2003 | Kreamer et al. |
| 2005/0010256 A1 | 1/2005 | Scharf |
| 2005/0209648 A1 | 9/2005 | Burnes et al. |
| 2006/0173369 A1 | 8/2006 | Kaski |
| 2007/0179542 A1 | 8/2007 | Prakash et al. |
| 2008/0125822 A1 | 5/2008 | Muessig et al. |
| 2008/0140147 A1 | 6/2008 | Husby |
| 2010/0076512 A1* | 3/2010 | Husby .............................. 607/17 |

OTHER PUBLICATIONS

"Minimizing Right Ventricular Pacing with a New Pacing Algorithm for Implantable Pacemakers and Defibrillators: ADI Mode,"0 Ellenbogen, EP Lab Digest, vol. 6, No. 3 (2006).

* cited by examiner

*Primary Examiner* — George Manuel
*Assistant Examiner* — Robert N Wieland

(57) ABSTRACT

An implantable medical device measures an AV delay in connection with measurement of N physiological patient parameters. The parameters are used for identifying a sub-space of an N-dimensional parameter space. An expected AV delay is assigned to the identified sub-space based on the measured AV delay, where the parameter space with expected AV delays constitute decision support information to be used by the device for performing a selective heart pacing. This selective pacing is performed based on a priori probability determined using the support information and a measured set of N parameters. The a priori probability represents the probability of successful AV conduction at a current patient condition determined based on the measured parameters.

16 Claims, 8 Drawing Sheets

METHOD AND IMPLANTABLE DEVICE FOR SELECTIVE HEART PACING

BACKGROUND OF THE INVENTION

1. Field of the Invention

The present invention generally relates to the provision of and usage of decision support information relating to selective heart pacing of implantable medical devices.

2. Description of the Prior Art

Lately a very hot topic within the field of implantable medical heart devices has been the promotion of intrinsic ventricular activity as far as possible, for instance when using so-called DDD pacemakers. When such a DDD pacemaker is implanted in, for example, a patient with atrioventricular (AV) block II or III, the DDD mode operation induces a situation very similar to left bundle branch block (LBBB) which in the long run may cause heart failure. As a consequence, there has been a trend to provide pacemakers with algorithms that minimize ventricular pacing. Such algorithms are, for instance, known as Ventricular Intrinsic Preference (VIP™) by St. Jude Medical, Managed Ventricular Pacing (MVP™) by Medtronic and AAIsafeR™ by Sorin.

These prior art algorithms work slightly differently but all have similar objectives—if an atrial event (P-wave) will lead to ventricular contraction, it should be left alone but if it does not invoke a ventricular contraction, the ventricle should be paced. The problem is that it is not known beforehand whether the P-wave will be blocked or not. In order to deal with this problem, the algorithms basically every now and then withhold the atrium triggered pacing and monitor the intrinsic AV interval.

However, every time the algorithms "listen" for intrinsic conduction, they let the heart perform in a non-optimal way if no conduction took place within an acceptable time period. This means that the long AV delays that will indeed occur during such listening periods with inferior conduction may introduce complications, such as non-physiologic PR intervals, pacemaker-mediated tachycardia and artificially limited maximum tracking rates as discussed in Kenneth A. Ellenbogen, "Minimizing right ventricular pacing with a new pacing algorithm for implantable pacemakers and defibrillators: ADI mode", *EP Lab Digest*, 6(3):18-21, March 2006.

SUMMARY OF THE INVENTION

There is therefore a need for a technique in identifying suitable periods during which "listening" for intrinsic contraction is appropriate and discriminating such periods for occasions where heart pacing instead should be performed.

It is a general object of the present invention to provide an implantable medical device and method that can generate decision support information reflective of expected AV delays for different patient conditions.

It is another object of the invention to provide complement information that is advantageously used in connection with VIP™, MVP™, AAIsafeR™ and other selective pacing algorithms.

Briefly, the present invention involves an implantable medical device, IMD, having a signal processor for detecting an intrinsic or induced atrial activity of a heart in a patient based on electric signals collected from the heart or from the IMD. A delay measurer measures an intrinsic AV delay defined as the time period from the detected atrial activity to any following intrinsic ventricular electric activity. In addition, a sensor arrangement measures N parameters representative of different physiological characteristics of the patient. These parameters are used by a sub-space processor for identifying a sub-space of multiple sub-spaces comprised in a N-dimensional parameter space. The measured AV delay is used by a delay assigner for assigning an expected intrinsic AV delay to the identified sub-space. The N-dimensional parameter space with the assigned expected AV delays constitutes decision support information that can be used by the IMD, for instance, in connection with a selective pacing algorithm.

In such a case, the sensor arrangement determines current values for the N parameters to get a representation of the current patient condition. The determined parameters are used by the sub-space processor for identifying a correct sub-space in the N-dimensional parameter space of the decision support information. A delay provider of the IMD provides an expected intrinsic AV delay associated with the identified sub-space. This provided AV delay is input to a probability estimator that generates an a priori probability estimate representing the probability of successful AV conduction for the current patient condition. The a priori probability estimate is used for controlling the selective pacing algorithm, basically by preventing generation and application of a ventricular pacing pulse if there is a high probability of AV conduction and triggering generation and application of the pacing pulse for a low AV conduction probability. In the former case, new statistics can be collected, i.e. AV delay, and be used for updating the decision support information.

The present invention also encompasses a method for generating decision support information and using the decision support information in selective ventricular pacing.

The embodiments provide valuable decision support information that can be used in connection with algorithms for minimal ventricular pacing by determining whether the algorithm should listen for and await intrinsic ventricular depolarization or postpone any such listening period until a later time when there is a higher probability of successful AV conduction.

Other advantages offered by the present embodiment will be appreciated upon reading the following description.

DESCRIPTION OF THE PREFERRED EMBODIMENTS

Figure 3:
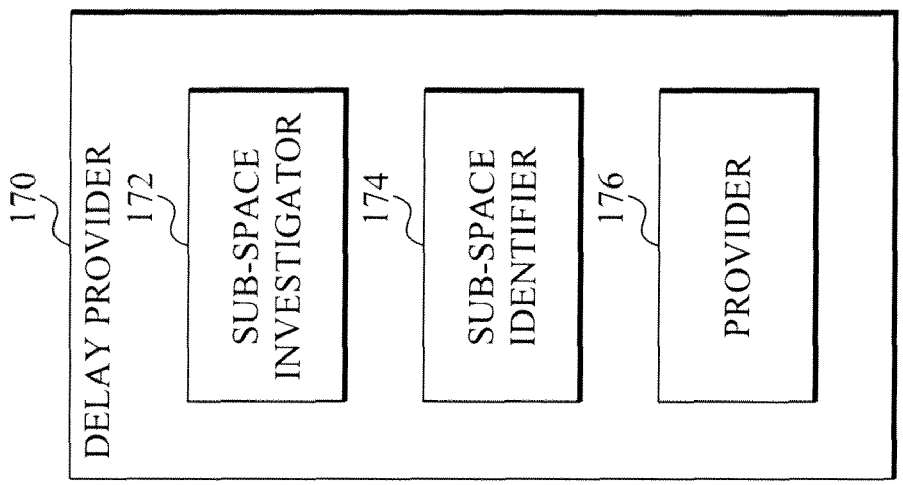
FIG. 3 is a schematic block diagram of an embodiment of the delay provider in FIG. 2.

Throughout the drawings, the same reference characters will be used for corresponding or similar elements.

The present invention generally relates to implantable medical devices and methods of operating such medical devices. In particular, the present invention provides a technique allowing identification of time periods that are suitable for listening to intrinsic electrical atrioventricular (AV) propagation and discriminate such periods from others where an induced or intrinsic atrial electric event will probably become blocked or the atrioventricular delay will at least be deleteriously long.

The present embodiments are therefore advantageously used as a complement to those IMD implemented algorithms that provides a selective pacing by minimizing ventricular pacing and favor intrinsic electric AV conduction, such as VIP™, MVP™ and AAIsafeR™.

When operated together with any such prior art algorithm, the embodiments provide decision support information that can be used for identifying suitable operational time periods during which the algorithms listen for electric AV propagation and hold any ventricular pacing. This will significantly improve the situation for the patient in that no such propagation listening is therefore scheduled to periods with expected low chance of intrinsic propagation as determined based on the decision support information. The risks associated with long AV delays that otherwise may occur with the prior art algorithms without the usage of the present invention, e.g. non-physiologic PR-intervals, pacemaker-induced tachycardia, artificially limited maximum tracking rate etc., are significantly reduced.

Figure 1:
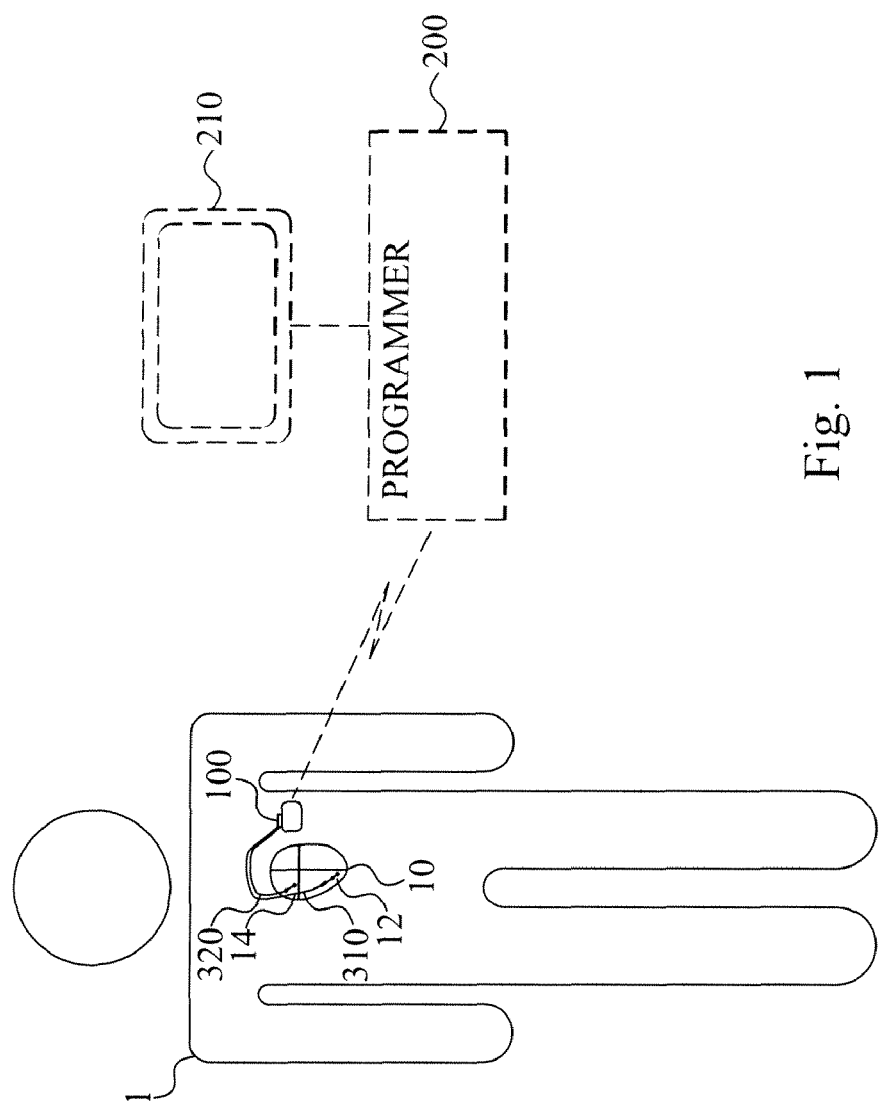
FIG. 1 is a schematic overview of a human subject equipped with an implantable medical device according to an embodiment.

FIG. 1 is a schematic overview of a human patient 1 having an implantable medical device, IMD, 100 as taught herein. In the FIG. 1, the IMD 100 is illustrated as a device that monitors and/or provides therapy to the heart 10 of the patient 1, such as a pacemaker, cardiac defibrillator or cardioverter. The IMD 100 is, in operation, connected to one or more, two in FIG. 1, intracardiac leads 310, 320 inserted into different heart chambers, the right atrium 14 and the right ventricle 12 in FIG. 1. The present invention is though not limited to right chamber leads 310, 320 but can also be used in connection with leads positioned in the left atrium or ventricle of the heart 10. Actually, also non-intracardiac leads, including epicardiac leads can also be used.

The patient 1 illustrated in FIG. 1 is a human patient 1. However, the present invention is not limited thereto, but can also be applied to IMDs 100 implanted in other animals, in particular other mammals.

FIG. 1 also illustrates an external programmer or clinician's workstation 200 that can communicate with the IMD 100. As is well known in the art, such a programmer 200 can be employed for transmitting IMD programming commands causing a reprogramming of different operation parameters and modes of the IMD 100. Furthermore, the IMD 100 can upload diagnostic data descriptive of different medical parameters or device operation parameters collected by the IMD 100. Such uploaded data may optionally be further processed in the programmer 200 before display to a clinician on a connected display screen 210. In the light of the present disclosure, such uploaded data can include the decision support information and other data relating to expected AV delays during different patient conditions. Data may also be downloaded from the programmer 200 to the IMD 100. Example of such data include standardized or default decision support information that is to be used by the IMD 100 before or together with IMD and patient specific decision support information.

Figure 2:
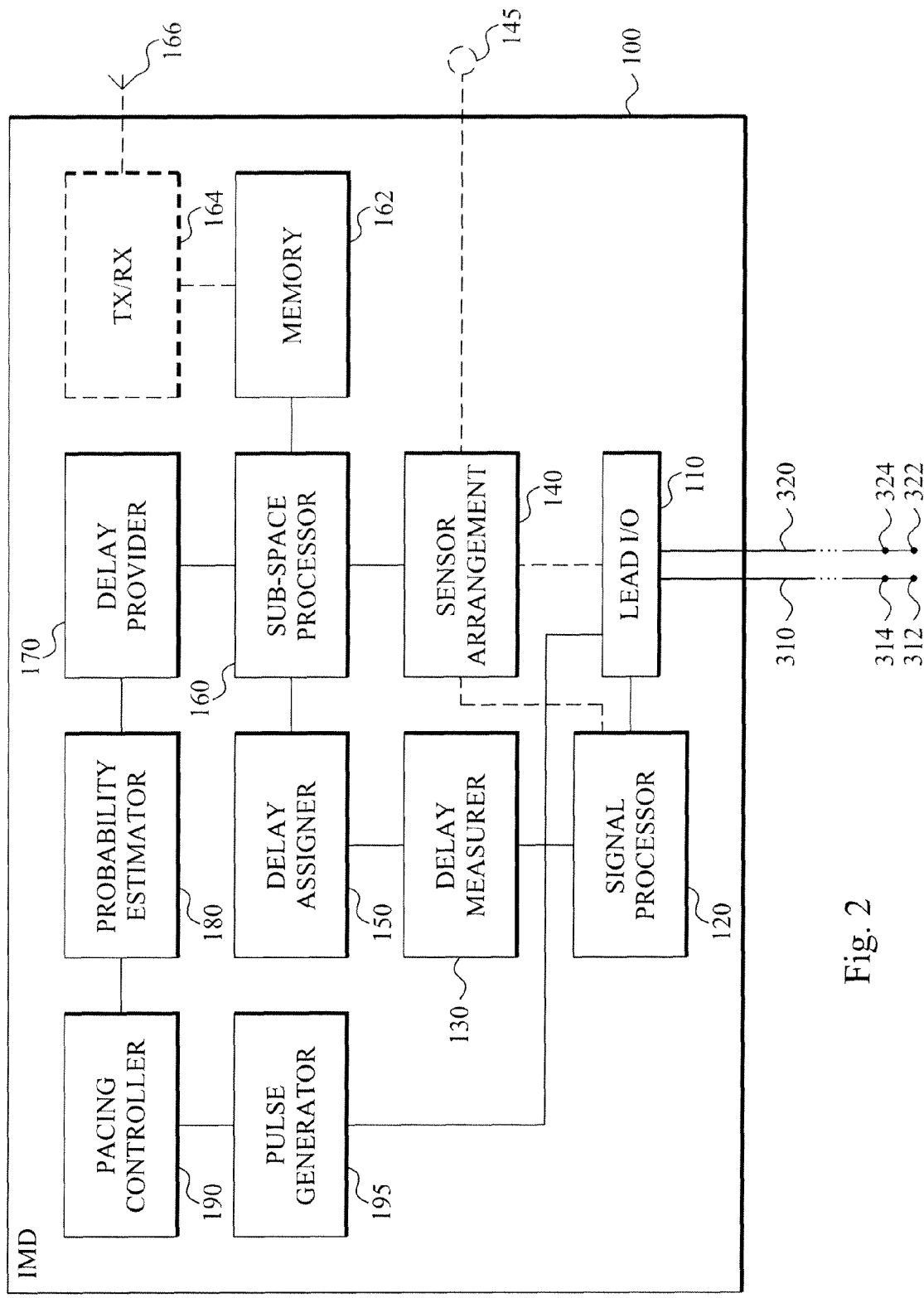
FIG. 2 is a schematic block diagram of an implantable medical device according to an embodiment.

FIG. 2 is a schematic block diagram of an IMD 100 according to an embodiment. The IMD 100 comprises a lead input/output (I/O) 110 that is, in operation, connectable to electrodes 312, 314, 322, 324 used for applying and sensing electric signals to and from the cardiac tissue of a subject. These electrodes 312, 314, 322, 324 are preferably arranged on one or more implantable medical leads 310, 320 connectable to the IMD 100 through the electrode input 110. As is well known in the art, such an implantable lead or catheter 310, 320 has a proximal end connected to the IMD 100 through the lead I/O 110. This IMD-connecting end presents one or more electric terminals that are in electric connection with the electrodes 312, 314, 322, 324 present on the opposite distal lead end, where the electric connection is achieved by electric conductors running along the length of the lead body. The distal lead end with its electrodes 312, 314, 322, 324 is then provided in connection with the heart tissue. For this purpose, the lead 310, 320 can include a tissue anchoring element, such as a helical fixation element, though other fixation elements, such as passive fixation elements, including fines, tines, etc., are also common. The fixation element can indeed constitute one of the electrodes of the lead 310, 320, while remaining electrodes can be ring electrodes, indifferent electrodes, tip electrodes, defibrillation electrode, or the like.

The IMD 100 can be connected to a single medical lead 310, 320, then preferably having at least two electrodes 312, 314, 322, 324. Alternatively, the IMD 100 is connected to multiple, i.e. at least two, implantable leads 310, 320 having electrodes. In either case, the at least one lead 310, 320 can be an intracardiac lead positioned in any of the chambers of the heart, such as right and/or left atrium and/or ventricle. Alternatively, the at least one lead 310, 320 could be epicardially positioned relative the heart. Also a combination of intracardial and epicardial leads is contemplated by the present invention. In a preferred embodiment, the IMD 100 and the lead I/O 110 are connected to a ventricular lead 310, such as right ventricular lead, and an atrial lead 320, preferably a right atrial lead.

In an implementation of the IMD 100, a signal processor 120 is arranged for processing an electric signal collected from the heart based on electrodes 322, 324 present on one of the leads 320, preferably an atrial lead. The signal processor 120 furthermore detects, based on the collected electric signal, an atrial electric activity or event of the heart. This detected atrial event corresponds to an intrinsic or induced atrial electric activity. In the former case, the intrinsic electric activity is the generation of a spontaneous electric signal by the atrium of the heart. Such an intrinsic atrial signal occurs during normal atrial depolarization, where the main electrical vector is directed from the SA (sinoatrial) node towards the AV node and spreads from the right atrium to the left atrium. This depolarization turns into a so-called P-wave on an ECG (electrocardiogram). Thus, in an embodiment, the detected electrical event is the intrinsic atrial depolarization as seen in the form of a P-wave.

In another embodiment, the atrial depolarization is induced by the IMD 100. In such a case, the IMD 100 includes a pulse generator 195 connected to the lead I/O 110. This generator 195 generates at least one atrial pacing pulse that is applied using electrodes 322, 324 of the atrial lead 320 to the atrium. In the art, such an IMD-induced electric atrial event is generally denoted A-wave as seen on an ECG. Thus, in this embodiment, the detected electric event is the induced atrial depolarization as seen in the form of an A-wave. No sensing of electric signals from the heart is required in this embodiment, as the signal processor 120 can determine the occurrence of an A-wave once the generator 195 has generated and applied an atrial pacing pulse.

A delay measurer 130 is implemented in the IMD 100 for measuring an intrinsic atrioventricular delay between the detected intrinsic or induced atrial electric activity and any following intrinsic ventricular electric activity or depolarization resulting in ventricular contraction. This delay detection is furthermore performed based on the electric signal collected by the lead 320 and processed by the signal processor 120. Thus, the delay measurer 130 determines the time from the detected or induced atrial electric activity, i.e. occurrence of a P/A-wave, to a detected intrinsic ventricular electric activity as sensed by electrodes 312, 314 of the ventricular lead 310 and processed by the signal processor 120. The measured time parameter is generally denoted AV delay in the art. Note that though the atrial event may indeed be induced by the IMD 100, the following detected ventricular event is, however, induced by the heart itself, i.e. is a so-called intrinsic ventricular depolarization.

The AV delay parameter measured by the delay measurer 130 can be expressed according to different embodiments. In a first embodiment, it is denoted as a number of seconds or milliseconds. Alternatively, it can be expressed as a number of samples that is the difference between the sample number for the detected intrinsic ventricular depolarization and the sample number for the detected intrinsic or atrial depolarization. If no ventricular depolarization is detected until a next atrial electric activity occurs, i.e. there is no propagation of the depolarization wave from the atriums to the ventricles, the measurer 130 can define the delay parameter according to a predefined value indicating that no following ventricular event occurred during that heart cycle.

A sensor arrangement 140 is provided in the IMD 100 for the purpose of measuring N parameters representative of N different physiological characteristics of the patient. This number N is equal to or larger than two. Thus, multiple parameters are monitored by the sensor arrangement 140 using sensor equipment 145; 312, 314; 322, 324 connected thereto. An example of such sensor equipment is the electrodes 312, 314; 322, 324 present on the leads 310, 320 connected to the lead I/O 110. These electrodes can be used for sensing and collecting different electric signals from the chambers of the heart. In such a case, the sensor arrangement 140 generates at least one physiologic parameter value from the sensed signals as is further discussed herein. Although, usage of electrodes 312, 314; 322, 324 present on connected medical leads 310, 320 are preferred examples of sensor equipment since no dedicated sensor units are required, the sensor arrangement 140 may be connected to a dedicated sensor unit 145 as schematically illustrated in FIG. 2.

In a preferred embodiment, the sensor arrangement 140 determines the N parameters in connection with measurement of the AV delay by the delay measurer 130. In such a case, the delay measurer 130 can send a trigger signal to the sensor arrangement 140 once it has determined the AV delay for the current heart cycle or indeed during the actual delay determination. The trigger signal then causes the arrangement 140 to perform a sensor reading and determination of the relevant N physiological parameters.

An alternative embodiment has a sensor arrangement 140 that generates the trigger signal upon measurement of the N parameters. The delay measurer 130 and/or signal processor 120 are then responsive to this trigger signal and performs the measurement and determination of an AV delay based on the signal.

In yet another embodiment, the delay measurer 130 and sensor arrangement 140 operate independently from each other and determines AV delays and N parameter values based on separate trigger events or according to independent sampling criteria. In such a case, the set of N parameters that are determined for a time period occurring at least in connection with the time period for which the AV delays was measured is preferably noted and used further herein.

Generally, the N parameters used in connection with the measured AV delay should reflect the N physiological characteristics of the patient at the time of the AV delay determination. This does, however, not necessarily imply that the parameters must be determined in parallel with the AV delay. In clear contrast, it is generally enough if the N parameters are determined in a time window centered at the AV delay measurement. This time window can be up to several tens of minutes but is preferably one or a few minutes or even no more than some seconds or tens of seconds.

The IMD 100 also includes a sub-space processor 160 connected to the sensor arrangement 140. This processor 160 uses the measured N parameters for identifying a sub-space among multiple sub-spaces that are embodied in a N-dimensional parameter space. The processor 160 therefore has access to, preferably in a connected data memory 162, data defining such a parameter space with multiple sub-spaces. In a typical implementation, the N parameters are quantified into different allowed parameter intervals. In such a case, the parameter space has $$\prod_{i=1}^{N} m_i$$

sub-spaces, where $m_i$ represents the number of allowed parameter intervals for a parameter i, i=1, . . . , N. The sub-space processor 160 identifies the sub-space among these $$\prod_{i=1}^{N} m_i$$

sub-spaces, which corresponds to or matches the particular parameter values that the sensor arrangement 140 determined.

Although usage of quantified parameter intervals leads to an efficient implementation of the organization and identification of sub-spaces in the N-dimensional parameter space, the embodiments are not limited thereto. In clear contrast, at least one of the parameters could be unquantified, thereby adopting any of the values from a minimum to a maximum parameter value.

A delay assigner 150 is connected to the delay measurer 130 and the sub-space processor 160. This assigner 150 assigns an expected intrinsic AV delay to the sub-space identified by the sub-space processor 160. This expected AV delay is furthermore determined by the assigner 150 based on the intrinsic AV delay determined by the delay assigner 150. In case no previous AV delay value has been assigned to the particular identified sub-space, the delay assigner 150 preferably simply determines the expected AV delay to be equal to the measured intrinsic AV delay and assigns it to the identified sub-space. However, if the identified sub-space contains at least one previously determined AV delay, the assigner 150 preferably determines the expected intrinsic AV delay as an average based on the AV delay from the delay measurer 130 and at least one of the previously determined and assigned AV-delays for that sub-space. In such a case, the average can be a simple average of all AV-delay values associated with the current sub-space. However, in a preferred embodiment, each AV delay previously assigned to the sub-space is preferably time-stamped in order to allow estimation of how recent the actual delay value is. In such a case, a weighted average of the delay values is preferably calculated by the delay assigner 150. Furthermore, the weights used in the averaging are preferably larger for more recent AV delays and smaller for older AV delays. The expected AV delay is therefore in this embodiment a time-weighted average of multiple AV delays.

The delay assigner 150 therefore preferably assigns the particular determined AV delay from the measurer 130 together with a time-stamp reflective of the time at which the AV delay was determined. In the case, the sub-space already contains at least one previous AV delay, it will now preferably include the expected AV delay, i.e. time-average of the at least one previous delay and the new AV delay, the individual AV delays and their associated time stamps.

The delay assigner 150 may furthermore remove identified AV delays associated with a currently identified sub-space if their time stamps have elapsed, indicating that they were measured very long ago and are therefore hardly relevant any more. Such a procedure allows the N-dimensional parameter space to include fresh AV delays that are relevant to the patient and do not reflect old and irrelevant data. Alternatively, the old and out-of-date values can be present in the decision support information but will merely have marginal, if any, influence on the expected AV delay due to the time-averaging as there weights will be small or even zero.

The N-parameter space therefore comprises assigned expected AV delays for at least some of its multiple sub-spaces. The parameter space with these assigned AV delays constitutes decision support information that can be used by the IMD 100 or some other unit in selective pacing of the heart. The updated parameter space is preferably stored in the connected memory 162, where it can be used by the IMD 100 in connection with activation of a depolarization propagation listening algorithm.

In addition to being a valuable tool for the IMD 100 itself as is further discussed herein, the decision support information constitutes valuable diagnostic information for the patient's physician. It can therefore be uploaded to an external unit, for instance the physician's programmer, upon receipt of a decision support request. The IMD 100 preferably comprises a transmitter and receiver (TX/RX) 164 with connected TX/RX antenna 166 that are used in the communication with the external unit. In such a case, the determined decision support information is fetched from the memory 162, processed by the transmitter 164 and then communicated by the antenna to the programmer.

The decision support information is preferably not a static information set. In clear contrast, it is preferably continuously, intermittently or periodically updated by the IMD 100 as new AV delay measurements and parameter value determinations are performed. This means that the IMD 100 can be configured for periodically or intermittently performing new delay and parameter measurements for the purpose of generating new data that can be used for updating or complementing the decision support information.

The IMD 100 can also be configured for performing new measurement for the purpose of complementing the decision support information at particular patient characteristics. Thus, if the sensor arrangement 140 notes, through the monitoring of at least one of the N physiologic patient parameters, that the at least one parameter reaches a value for which no previous delay measurements have been performed, it preferably triggers the delay measurer 130 for conducting such a measurement. The delay assigner 150 then updates the decision support information by assigning the new AV delay to the relevant sub-space identified by the sup-space processor 160.

Generally, if the IMD 100 can operate according to the VIP™, MVP™, AAIsafeR™ or some similar selective pacing algorithm, the IMD 100 preferably performs delay and parameter measurements during the periods where the algorithm holds any ventricular pacing and instead listens for intrinsic AV depolarization propagation. The decision support information of the invention is therefore advantageously generated and updated during such periods of activation of the VIP™, MVP™, AAIsafeR™ algorithms.

Figure 12:
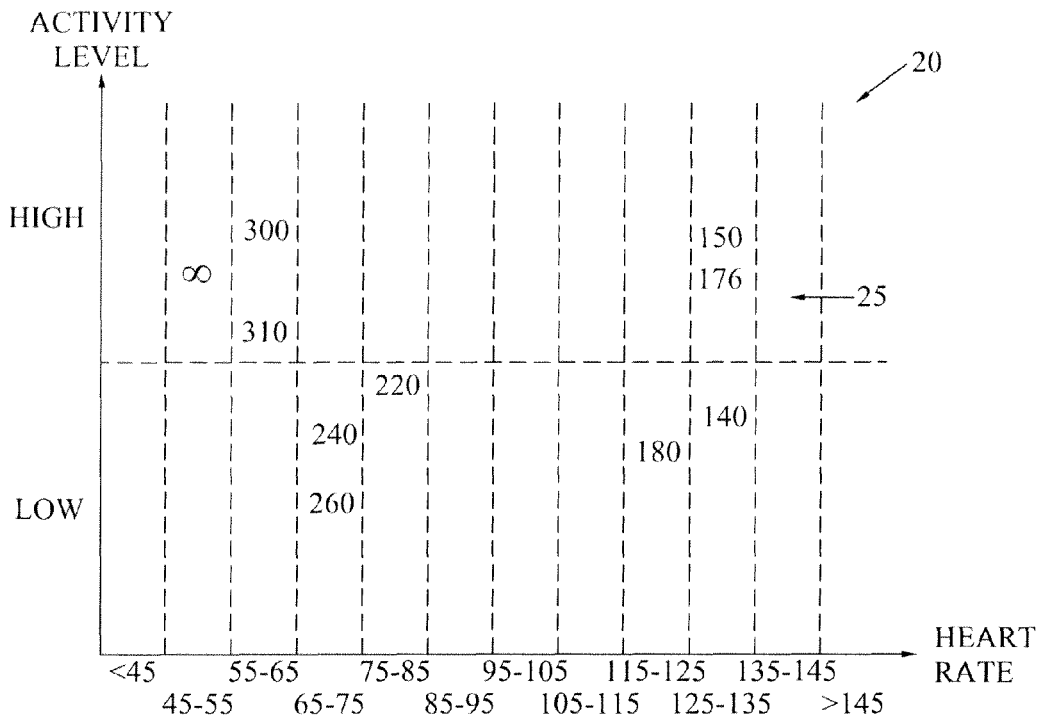
FIG. 12 is diagram illustrating a N-dimensional parameter space with expected atrioventricular delays assigned to different sub-spaces.

FIG. 12 gives an illustrative presentation of an example of how the decision support information can look like. In this example, two parameters, heart rate and activity level of the patient, are monitored by the sensor arrangement. Furthermore, the activity level has a coarse quantification into low and high activity. A finer quantification is used for the heart rate, where the possible rate values are divided into regions of 10 beats per minutes. The 2D parameter space 20 is therefore divided into 24 sub-spaces 25 in this example. As is seen in FIG. 12, some of the sub-spaces 25 have no assigned expected intrinsic AV delay. The reason for this is that no AV delay measurements have yet been conducted at the particular physiological patient condition represented by these sub-spaces 25. Other sub-spaces have a single assigned AV delay, which is used as the expected intrinsic AV delay for those sub-spaces 25. Three of the sub-spaces have more than one assigned value and the expected intrinsic AV delay for those sub-spaces is preferably a weighted average of the respective AV delays.

In FIG. 12, the sub-space corresponding to high activity level and a heart rate in the interval 45-55 bpm has an indication of ∞ corresponding to "infinitive" AV delay, i.e. no intrinsic ventricular depolarization was detected following the intrinsic/induced atrial depolarization during the AV delay measurements.

The IMD embodiment described above comprises functionality for generating and updating decision support information. This decision support information is preferably also used by the IMD 100. Alternatively, the IMD 100 merely determines and updates the information and then uploads it to the programmer for statistical purposes. Furthermore, such uploaded information can indeed be used by other IMDs as starting or default decision support information that can be later updated by the IMD once they have performed some delay and parameter measurements. This means that the support information generation does not necessarily have to start from an empty N-parameter space. In clear contrast, the parameter space can be filled with some intrinsic AV delay values for at least some of the sub-spaces. Such an approach will probably not give accurate and relevant AV delays for the different sub-spaces if they are collected from a single other patient. However, if multiple IMD patients generate decision support information according to the invention and upload the information to the physician, he/she can generate default support information based on the data collected by the multitude of patients. Even though such a default information may be less relevant than the decision support information generated by the IMD itself in a patient, it may still be valuable as starting material when updating the decision support information with data determined by the IMD itself. In such a case, AV delays collected by the IMD are preferably weighted higher than already present default AV delays assigned to some of the sub-spaces.

When the IMD 100 is to use the decision support information for its operation, the sensor arrangement 140 measures the N parameters representing the N different physiological characteristics of the patient as previously described. The sub-space processor 160 uses the particular values for the measured parameters to identify a sub-space in the N-dimensional parameter space of the decision support information.

The IMD 100 preferably comprises a delay provider 170 connected to the sub-space processor 160 and arranged for providing an expected intrinsic AV delay associated with the sub-spaced identified by the processor 160. The provider 170 preferably reads and fetches the value associated with the relevant sub-space from the decision support information as stored in the memory 162.

A probability estimator 180 uses the provided expected intrinsic AV delay reflective of the current patient condition to estimate an a priori probability that a detected intrinsic or induced atrial electric activity of the heart will trigger intrinsic ventricular electric activity, i.e. depolarization, leading to ventricular contraction within a target AV delay. In a typical embodiment, probability estimator 180 compares the expected AV delay from the delay provider 170 with a threshold AV delay or the target AV delay. In such a case, the a priori probability can be in the form of a simple yes or no. Thus, if the expected AV delay is larger than the threshold delay, the estimator 180 determines the a priori probability to be zero, implying that there is zero expected probability that an intrinsic/induced atrial depolarization will, during the current patient conditions as determined by the N parameters, propagate into ventricular depolarization and trigger ventricular contraction. However, if the expected AV delay does not exceed the threshold delay, the estimator 180 determines that there is 100% expected probability that an intrinsic/induced atrial event will propagate into a following ventricular event within the target AV delay.

Of course more elaborated embodiments can be used for the a priori probability than a simple no, e.g. $0_{bin}$ or 0%, and yes, e.g. $1_{bin}$ or 100%. In such a case, the particular a priori probability estimate is dependent on how much the expected AV delay from the delay provider 170 differs from the target AV delay. For instance 100% expected propagation if $T_{AV}^{exp} < 0.5 T_{AV}$, 75% propagation if $0.5 T_{AV} \leq T_{AV}^{exp} < 0.75 T_{AV}$, 50% propagation if $0.75 T_{AV} \leq T_{AV}^{exp} < T_{AV}$, 25% propagation if $T_{AV} \leq T_{AV}^{exp} < 1.25 T_{AV}$ and 0% propagation if $T_{AV}^{exp} \geq 1.25 T_{AV}$, where $T_{AV}^{exp}$ represents the expected intrinsic AV delay and $T_{AV}$ the target AV delay.

The target delay used by the estimator 180 may be fixed for a particular IMD 100 and patient. The target value can then be programmed into the IMD 100 by a physician before or at the time of implantation or be downloaded into the IMD 100 after implantation. In an alternative approach, the target delay value is not fixed but is instead adjusted based on where in the parameter space the patient's current condition corresponds to. Thus, this embodiment basically teaches usage of different target values adapted for usage in connection with different sub-spaces. For instance, in connection with FIG. 12, a first target delay is used if the heart rate is below 75 bpm, a second target delay is used in the interval 75-125 bpm and a third target delay is applicable if the heart rate parameter is above 125 bpm. Usage of such an adaptive thresholding generally improves the accuracy in the a priori probability estimation.

The IMD 100 also has a pacing controller 190 that is connected to the estimator 180 and uses the a priori probability data therefrom. This controller 190 controls the operation and activation of a connected pulse generator 195. The generator 195 generates a heart pacing pulse that is applied to the heart using electrodes 312, 314; 322, 324 of the connected medical leads 310, 320. In particular, the pulse generator 195 is adapted for generating, in this context, a pacing pulse or pulse train to be applied to at least one ventricle of the heart to induce ventricular contraction.

The operation of this pulse generator 195 is controlled by the pacing controller 190 in that the generator 195 preferably generates and applies, through the lead I/O 110 and at least one lead 310, 320, the ventricular pacing pulse based on the control signal from the controller 190. The controller 190 is in turn responsive to the a priori probability from the probability estimator 180. As a consequence, a selective pacing pulse generation and application based on the a priori probability is obtained.

Thus, if the a priori probability indicates that there is low probability that a sensed intrinsic or induced atrial electric activity will propagate into a corresponding intrinsic ventricular electric activity as determined by the a priori probability, the pacing controller 190 preferably generates the control signal activating the pulse generator 195 and causing the application of an induced ventricular pulse. Correspondingly, if the a priori probability indicates that it is highly likely that the intrinsic/induced atrial activity will propagate into an intrinsic ventricular activity, the pacing controller 190 preferably does not generate any generator activating control signal. In clear contrast, the atrial electric event is allowed to propagate into an expected following ventricular event.

Figure 11:
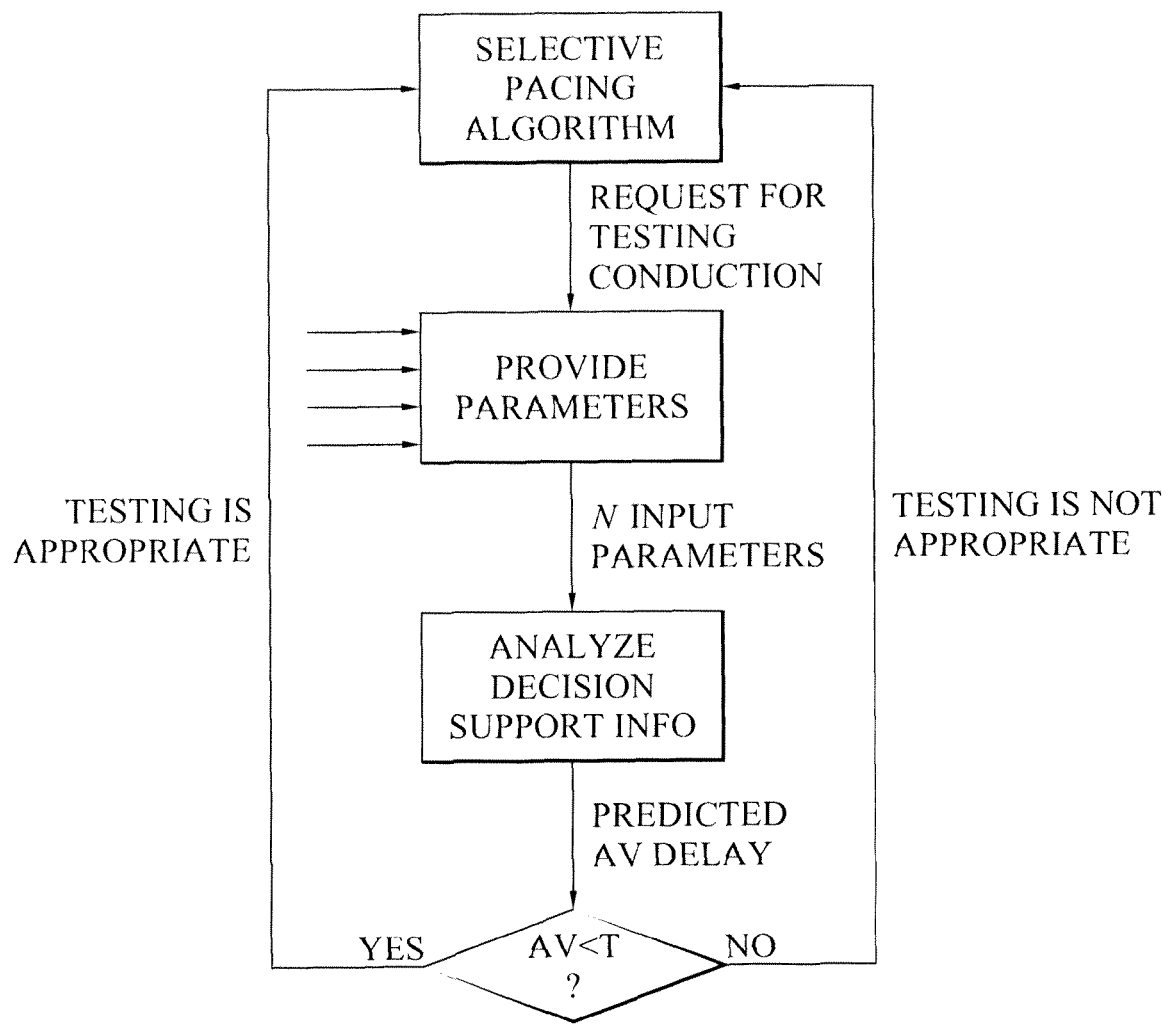
FIG. 11 is a schematic illustration of the usage of an embodiment in connection with Ventricular Intrinsic Preference algorithm.

When used in connection with a VIP™, MVP™ or AAIsafeR™ algorithm, the IMD 100 therefore identifies those physiological patient conditions that correlate with expected atrial-to-ventricular electric conduction and other conditions where there is an expected AV block or at least a very prolonged AV delay. With reference to FIG. 11, when the algorithm is initiated, the IMD 100 of the invention starts a conduction test as previously described by collecting the N parameter values. These values are used for identifying the relevant sub-space in the decision support information and an associated expected intrinsic AV delay correlating with the current physiological patient condition is provided. If this expected AV delay is within the target delay and therefore there is a high a priori probability of AV conduction, the current situation is appropriate for performing the algorithm. The algorithm therefore temporarily prevents any ventricular pacing and instead allows the induced/intrinsic electric atrial depolarization to propagate into the ventricle. Furthermore, during this listening period, the IMD 100 may collect further data, i.e. AV delay data measured by delay measurer and parameter data from the sensor arrangement 140 for the purpose of updating the decision support information.

However, if the expected intrinsic AV delay exceeds the target AV delay and there is low a priori probability of AV conduction, the algorithm is prevented from being activated and instead ventricular pacing pulses are delivered.

Thus, the present embodiments are therefore advantageously used as a complement to the VIP™ and other conduction testing algorithms for the purpose of identifying suitable periods to hold any ventricular pacing and instead listen for AV conduction and ventricular depolarization.

The units 110 to 195 of the IMD 100 can be implemented in hardware, software of a combination of hardware and software.

FIG. 3 is a schematic block diagram of an embodiment of the delay provider in the IMD of FIG. 2. In a typical implementation, the delay provider 170 provides the expected intrinsic AV delay assigned to the sub-space identified by the sub-space processor based on the determined parameters. This expected AV delay could be a single value assigned to the sub-space or a (weighted) average of multiple AV delays assigned to the sub-space. However, a situation can arise when there is actually no AV delay assigned to the relevant sub-space in the decision support information. This happens when no prior measurements have been conducted at a situation where the current physiologic characteristics of the patient are met. In such a case, a neighboring sub-space delay can be used.

Figure 13:
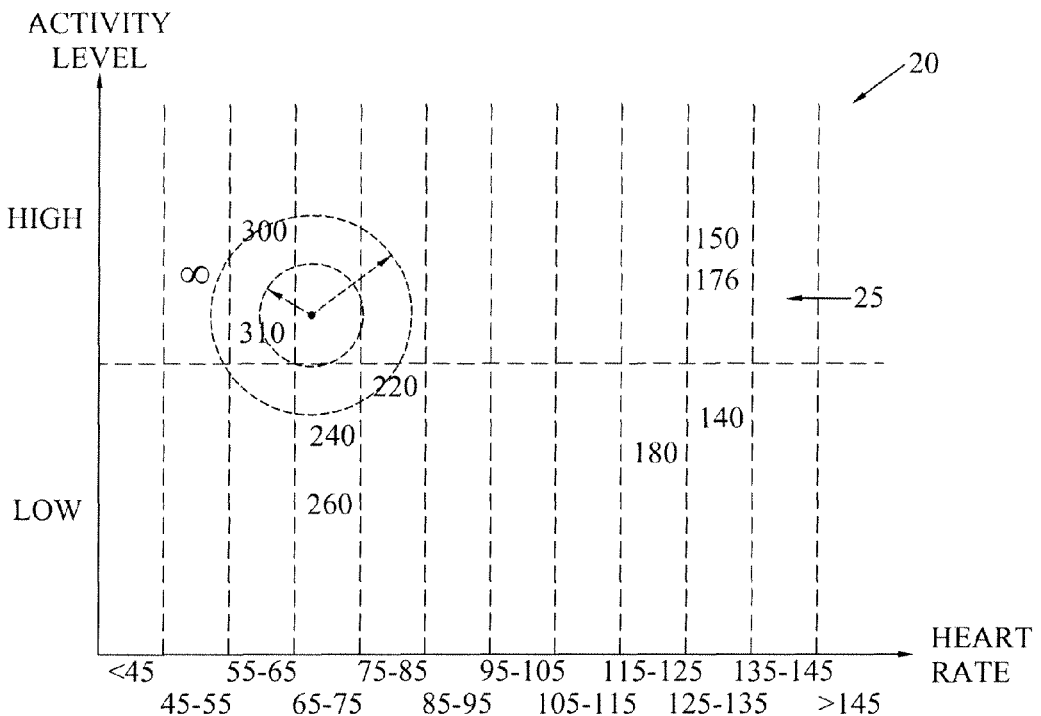
FIG. 13 schematically illustrates an embodiment of identifying an atrioventricular delay for a sub-space.

The delay provider 170 therefore includes a sub-space investigator 172 for investigating whether the identified sub-space has any assigned intrinsic AV delay. If there are one or more such delays in the sub-space, a provider 176 provides the expected AV delay for the sub-space based on at least a portion of the values. However, if no AV delay has been assigned to the sub-space, a sub-space identifier 174 is activated for identifying a sub-space in the N-dimensional parameter space having an assigned intrinsic delay. Furthermore, this sub-space preferably minimizes the Euclidian distance in the parameter space to the sub-space identified based on the N input parameters. FIG. 13 illustrates this concept. Assume that the current parameters indicate a patient condition of high patient activity and a heart rate of 67.5 bpm. No AV delay has been assigned to this particular sub-space in the decision support information. The Euclidian distances to neighboring or other sub-spaces in the 2D space are determined. In this case, the closest assigned AV delay occurred at a patient condition with high activity level and 61 bpm. The provider 176 therefore provides the AV delay value, i.e. 310 ms, minimizing the distance to the current point in the parameter space and use it as expected AV delay for the current sub-space.

The units 172 to 176 of the delay provider 170 can be implemented in hardware, software of a combination of hardware and software. The units 172 to 176 may all be implemented in the delay provider 170. In an alternative implementation, at least one of the units 172 to 176 is arranged elsewhere in the IMD.

Figure 4:
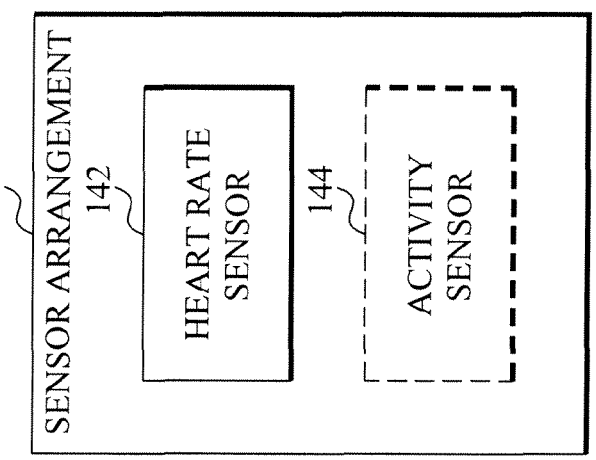
FIG. 4 is a schematic block diagram of an embodiment of the sensor arrangement in FIG. 2.

FIG. 4 is a schematic block diagram of an embodiment of the sensor arrangement 140 in the IMD of FIG. 2. This embodiment determines the two parameters indicated in the diagrams of FIGS. 12 and 13. Thus, the arrangement 140 comprises a heart rate sensor 142 arranged for measuring a current heart rate of the patient's heart. This rate sensor 142 preferably uses electric signals collected by the electrodes of the leads connected to the IMD for determining the heart rate according to well-known techniques.

Another preferred parameter to use according to the invention and having a correlation to expected AV delay is the patient activity. The sensor arrangement 140 therefore preferably comprises an activity sensor 144. There are several different activity sensors 144 known in the art that can be used according to the invention. For instance, accelerometers, motion transducers, including piezo-based transducers, heart rate sensors, respiratory rate sensors, respiratory depth sensor etc. can be used and are all well-known in the art.

The units 142 and 144 of the sensor arrangement 140 can be implemented in hardware, software of a combination of hardware and software. The units 142 and 144 may all be implemented in the sensor arrangement 140. In an alternative implementation, at least one of the units 142 and 144 is arranged elsewhere in the IMD.

Although usage of two parameters for spanning the parameter space of the decision support information has been discussed herein and illustrated in FIGS. 12 and 13 the present invention is not limited thereto. In clear contrast more than two parameters that are reflective of physiological characteristics of the patient that correlate with expected AV delays can be used according to the invention. Such other parameters include body posture, as determined by a posture sensor, minute ventilation, stroke volume, left ventricular pressure (LVP), left atrial pressure (LAP), right ventricular pressure (RVP), arterial oxygen level, venous oxygen level, etc.

Figure 5:
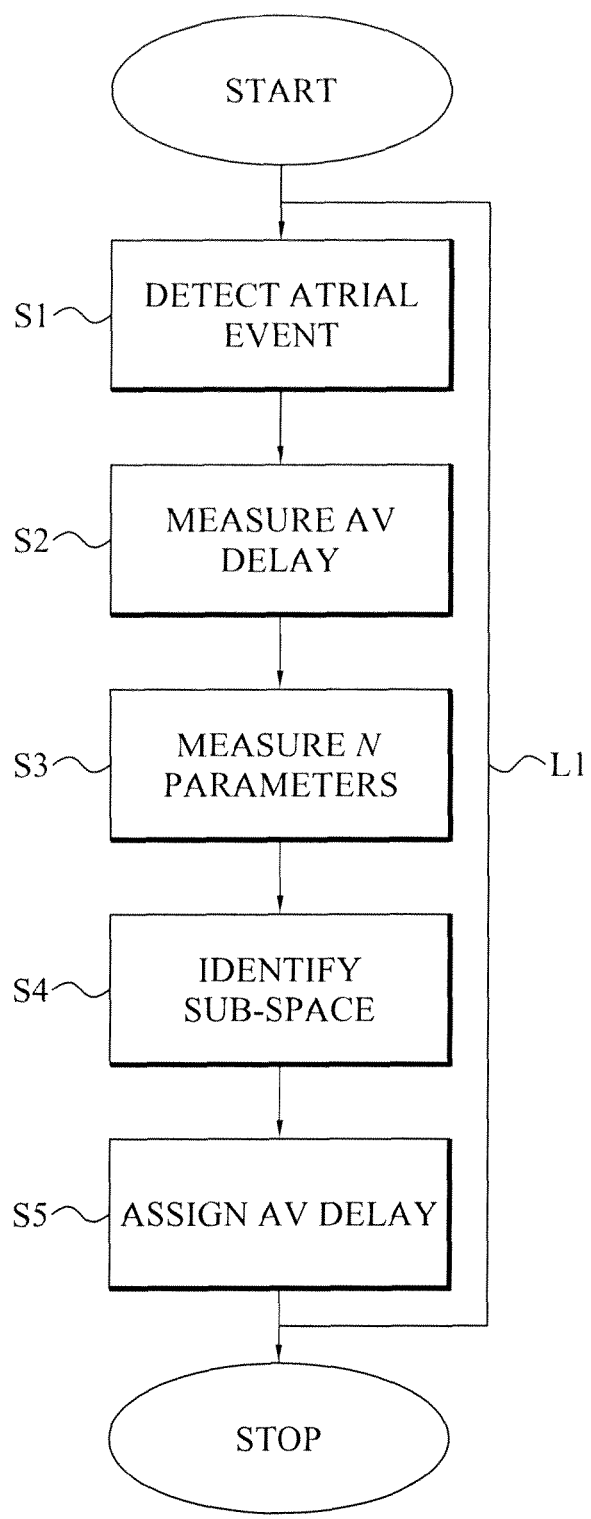
FIG. 5 is a flow diagram a method for generating pacing decision support information according to an embodiment.

FIG. 5 is a flow diagram illustrating a method of generating decision support information, for instance, for use in a selective heart pacing. The method starts in step S1, where an intrinsic (P-wave) or induced (A-wave) atrial electric activity of the heart is detected. A next step S2 measures the AV delay defines as the period of time from the detected atrial event to a following intrinsic ventricular electric activity. Step S3 measures N multiple parameters representative of different physiological characteristics of the patient. This step S3 may be conducted following step S2 as illustrated in FIG. 12. In alternative implementations, step S3 may be performed before or in parallel with step S2.

A next step S4 identifies a sub-space of multiple sub-spaces in a N-dimensional parameter space. Step S4 is furthermore performed based on the N parameters measured in step S3. An expected intrinsic AV delay is assigned in step S5 to the sub-space identified in step S4. This expected intrinsic AV delay is furthermore determined at least partly based on the AV delay measured in step S2. The N-dimensional parameter space with assigned expected intrinsic AV delay constitutes the decision support information.

In a preferred embodiment, the decision support information is preferably updated or complemented during operation of the IMD, which is schematically illustrated by the line L1. As a consequence, new AV delay and parameter measurements are used for adding more expected AV delay and/or update the previous expected AV delays of the decision support information.

Figure 6:
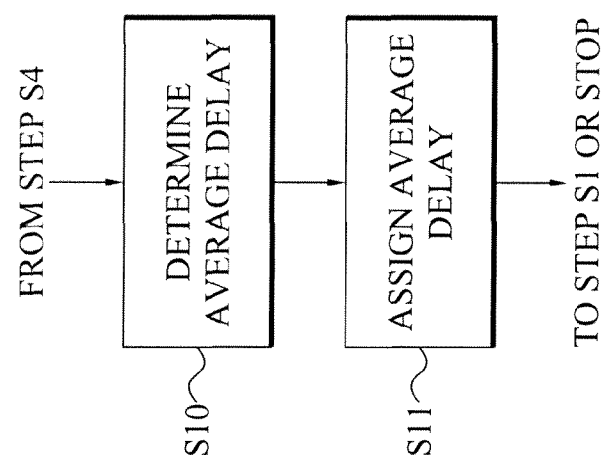
FIG. 6 is a flow diagram illustrating an embodiment of the delay assigning step of FIG. 5.

FIG. 6 is a flow diagram illustrating an embodiment of the assigning step S5 of FIG. 5. The method continues from step S4 of FIG. 5. In a next step S10, an average delay is determined based on the measured delay from step S2 of FIG. 5 and at least one other AV delay that has previously been measured and assigned to the current sub-space. The average is preferably a weighted average, $$T_{AV}^{exp} = \sum_j w_j T_{AV}^j,$$

where $w_j$ denotes delay weights and $T_{AV}^j$ designates a measured AV delay. The weights $w_j$ are preferably selected so that more recently measured AV delays are weighted heavier than older AV delays. The calculated average value is then assigned as expected intrinsic AV delay in step S11 for the current sub-space. The original AV delay values used for calculating the average are preferably stored for the sub-space in order to allow updating of the weighted average value without averaging errors when further delays relevant for the sub-block become available. The method then ends or continues to step S1 of FIG. 5 for conducting a new AV delay measurement.

Figure 7:
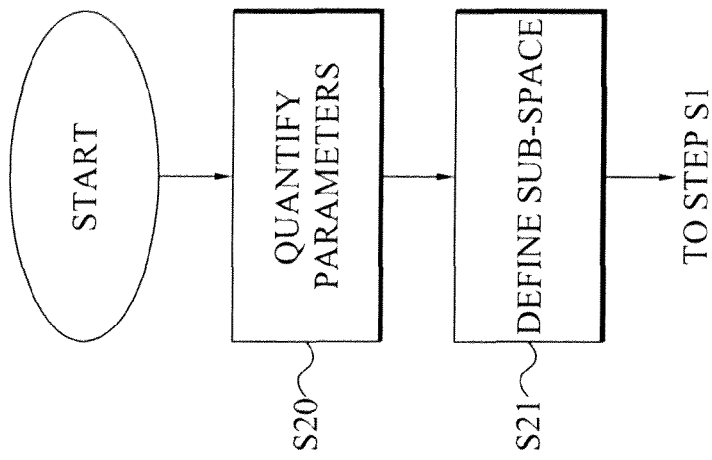
FIG. 7 is a flow diagram illustrating additional steps of the information generating method of FIG. 5.

FIG. 7 is a flow diagram illustrating additional steps of the method of generating decision support information. The method starts in step S20, where the range of possible parameter values is quantified into a number of allowed parameter intervals. Each sub-space is then associated with the respective interval in the N parameters in step S21. Not all of the N parameters need to be quantified in step S20, even though such a procedure is preferred and simplifies the definition of sub-spaces. The level of quantification can be the same of different for the N parameters and can range from a coarse quantification, i.e. merely two or few parameter intervals, into finer quantification using multiple intervals. The method then continues to step S1 of FIG. 5.

Figure 8:
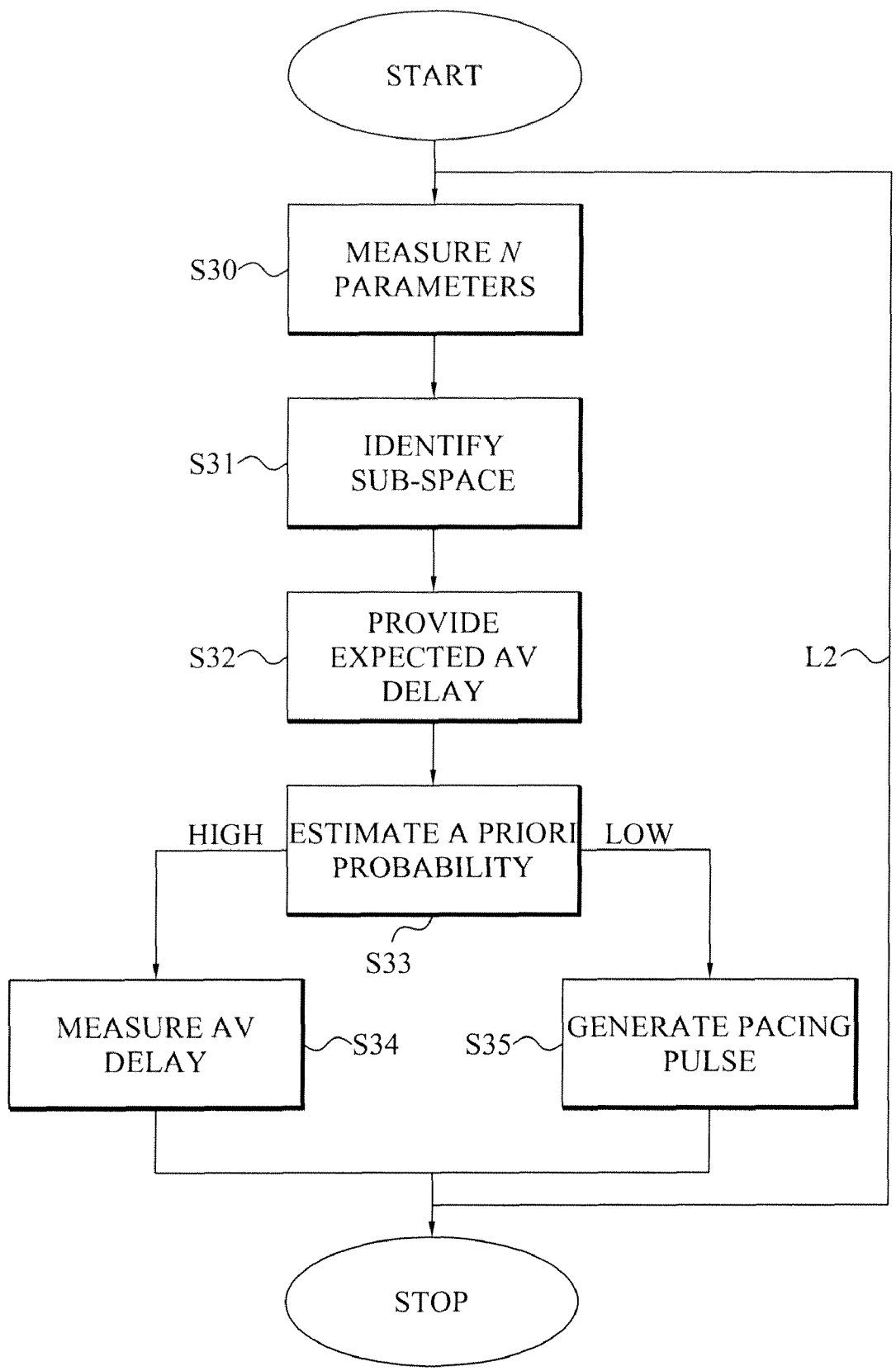
FIG. 8 is a flow diagram illustrating a method for selectively pacing a heart according to an embodiment.

FIG. 8 is a flow diagram illustrating a method of selectively pacing a heart of a patient based on the decision support information and, for instance, generated according to the method disclosed in FIG. 5. The method starts in step S30, where N parameters descriptive of different physiological patient characteristics are measured. This step S30 is conducted similar to step S3 of FIG. 5.

A next step S31 identifies a current sub-space in the N-dimensional parameter space of the decision support information based on the measured parameters. This identification is basically conducted as previously described in connection with step S4 of FIG. 5. An expected AV delay associated with the identified sub-space is provided in step S32 from the decision support information.

An a priori probability representative of the probability that an intrinsic/induced atrial electric activity will propagate into a corresponding intrinsic ventricular electric activity within a target AV delay for the current patient condition is estimated in step S33. This estimation of step S33 is performed based on the expected AV delay provided in step S32. The estimation preferably uses a comparison of the particular value of the provided expected AV delay and a threshold delay, preferably the target AV delay. Thus, if the expected AV delay is smaller than the target delay, there is a high probability of atrial-to-ventricular conduction. In such a case, the actual AV delay is preferably measured in step S34. The decision support information can therefore be updated based on this newly acquired AV delay. The relevant sub-space can be the one recently identified in step S31, thereby relaxing the need for a further parameter measurement and sub-space identification.

However, if the expected AV delay exceeds the target delay and there is a low probability of any AV conduction for the current patient condition, the selective pacing algorithm preferably generates a pacing pulse that is applied to the heart of the patient, preferably to at least one ventricle of the heart in step S35.

In other words, in step S34 intrinsic ventricular activity is allowed to occur with a preferred updating of the decision support information, whereas in step S35 induced ventricular activity occurs with no information updating.

In order to further update the decision support information, in particular for those sub-spaces that have long expected intrinsic AV delays and probably would result in a decision to go from step S33 to step S35 in FIG. 8, the pulse generation of step S35 may be temporarily switched off even though the a priori probability indicates low probability of AV conduction. In such a case, the IMD listens for any following ventricular activity and contraction and measures the AV delay. The decision support information is then updated based on this AV delay. This is advantageous in some situations in order to complement the decision support information with more data and in particular more recent data. Thus, the IMD can select to sometimes, such as every $5^{th}$ or $10^{th}$ time override the decision to pace based on the a priori probability.

Figure 9:
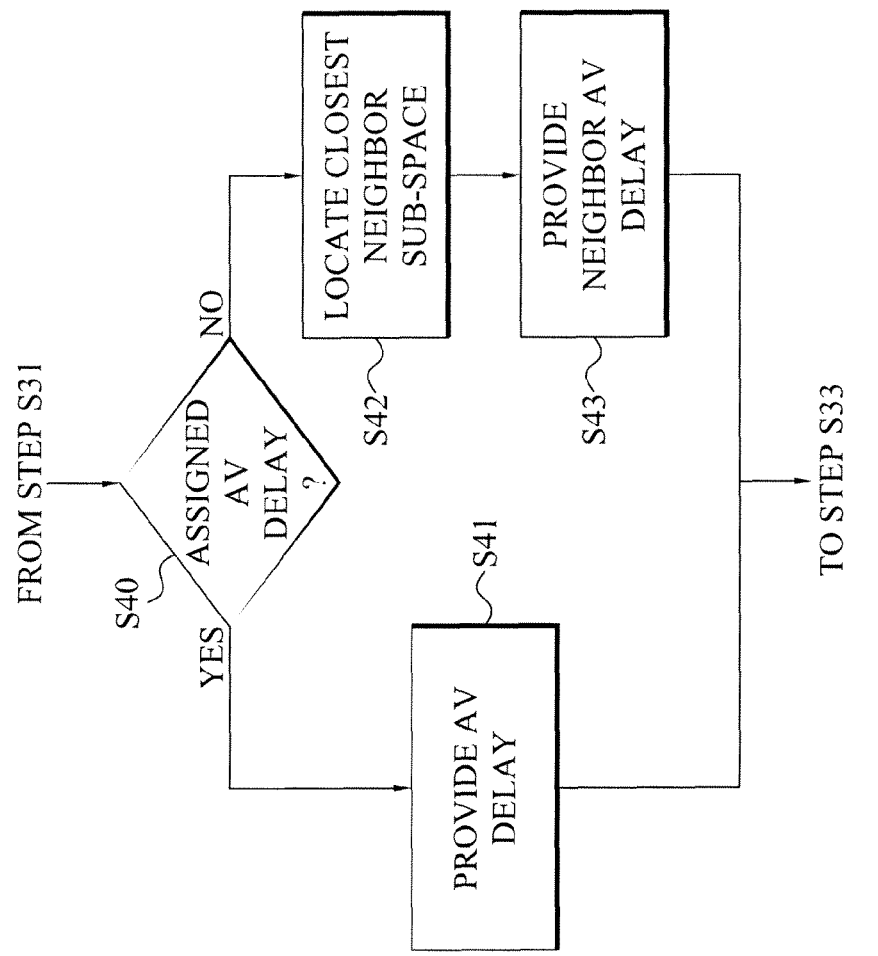
FIG. 9 is a flow diagram illustrating an embodiment of the delay providing step of FIG. 8.

FIG. 9 is a flow diagram illustrating an embodiment of the delay providing step S32 of FIG. 8. The method continues from step S31 of FIG. 8. A next step S40 investigates whether any AV delay value has previously been assigned to the current sub-space. In such a case, the method continues to step S41, where the assigned AV delay or an average of multiple assigned AV delay is provided as the expected intrinsic AV delay for the current sub-space. However, if there is not previously assigned delay value for the current sub-space, the method continues to step S42. This step S42 locates a closest neighboring sub-space in the N-dimensional parameter space. The sub-space is preferably the sub-space in the parameter space that minimizes the Euclidian distance to the current sub-space. Furthermore, the sub-space located in step S42 has at least one previously assigned AV delay. The AV delay or average of AV delays of the located sub-space is provided in step S43 and used as expected intrinsic AV delay for the current sub-space. The method then continues to step S33 of FIG. 8.

Figure 10:
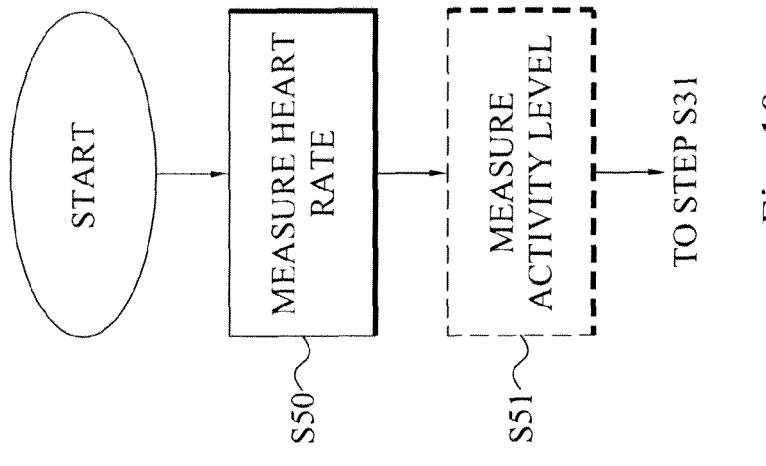
FIG. 10 is a flow diagram illustrating embodiments of the parameter measuring step of FIG. 8.

FIG. 10 is a flow diagram illustrating an embodiment of step S30 in FIG. 8. The method starts in step S50, where the current heart rate of the patient is estimated. This rate estimation is preferably performed based on measured electric signals collected by the IMD from the heart. If the heart is currently paced, the heart rate can alternatively be determined directly by the IMD from the pacing rate without any need for signal sensing. A next step measures a current physical activity level of the patient, preferably using accelerometers or similar activity sensors. The heart rate and activity level data are used in step S31 of FIG. 8 as input parameters for identifying a relevant sub-space.

The operation of step S51 may be conducted following step S50 as illustrated in FIG. 10. Alternatively, step S51 can be performed before or in parallel relative step S50.

Although modifications and changes may be suggested by those skilled in the art, it is the intention of the inventor to embody within the patent warranted heron all changes and modifications as reasonably and properly come within the scope of his contribution to the art.

The invention claimed is:

1. An implantable medical device comprising:
   an electric signal processor configured to process an electric signal and to detect, based on said electric signal, an intrinsic or induced atrial electric activity of a heart of a subject;
   a delay measurer configured to measure, based on said electric signal, an intrinsic atrioventricular delay between said detected intrinsic or induced atrial electric activity and any following intrinsic ventricular electric activity of said heart;
   a sensor arrangement that measures N parameters representative of N different physiological characteristics of said subject, where $N \geq 2$;
   a sub-space processor configured to identify, based on said measured N parameters, a sub-space of multiple sub-spaces comprised in a N-dimensional parameter space; and
   a delay assigner configured to assign an expected intrinsic atrioventricular delay to said identified sub-space based on said measured intrinsic atrioventricular delay, wherein said N-dimensional parameter space with assigned expected intrinsic atrioventricular delays constitutes decision support information for use in a selective pacing of said heart, wherein said delay assigner is configured to i) determine a time-weighted average of said measured intrinsic atrioventricular delay and at least one previously measured intrinsic atrioventricular delay assigned to said identified sub-space, and ii) assign said time-weighted average to said identified sub-space.

2. An implantable medical device comprising:

a sensor arrangement that measures N parameters representative of N different physiological characteristics of a subject, where N≧2;

a sub-space processor configured to identify, based on said measured N parameters, a sub-space of an N-dimensional parameter space comprising multiple sub-spaces, where at least a portion of said multiple sub-spaces has a respective assigned expected intrinsic atrioventricular delay;

a delay provider configured to provide an expected intrinsic atrioventricular delay associated with said identified sub-space;

a probability estimator configured to estimate an a priori probability that an intrinsic or induced atrial electric activity of a heart of said subject will trigger intrinsic ventricular electric activity within a target atrioventricular delay based on said expected intrinsic atrioventricular delay;

a pacing pulse generator that generates a heart pacing pulse based on a control signal; and a pacing controller configured to selectively generate, based on said estimated a priori probability, said control signal activating said pacing pulse generator.

3. The device according to claim 2, wherein said delay provider comprises:

a sub-space investigator that investigates whether said identified sub-space has an assigned intrinsic atrioventricular delay;

a sub-space identifier that locates, if said identified sub-space has not any assigned intrinsic atrioventricular delay, a sub-space having an assigned intrinsic atrioventricular delay and minimizing an Euclidian distance in said N-dimensional parameter space to said identified sub-space; and a provider that provides said intrinsic atrioventricular delay of said located sub-space.

4. The device according to claim 2, wherein said probability estimator estimates said a priori probability based on a comparison of said expected intrinsic atrioventricular delay and a threshold delay.

5. The device according to claim 2, wherein said pacing controller is configured to i) generate said control signal activating said pacing pulse generator to generate a heart pacing pulse if said a priori probability indicates a low probability of triggering ventricular contraction, and ii) omit generation of any control signal if said a priori probability indicates a high probability of triggering ventricular contraction.

6. The device according to claim 2, further comprising a delay measurer configured to measure a delay between a detected intrinsic or induced atrial electrical activity of said heart and any following intrinsic ventricular contraction if said a priori probability indicates a high probability of triggering ventricular contraction.

7. The device according to claim 6, wherein said sensor arrangement comprises:

a heart rate sensor that measures a current heart rate of said heart; and an activity sensor that measures a current physical activity level of said subject.

8. The device according to claim 1, wherein said sensor arrangement comprises:

a heart rate sensor that measures a current heart rate of said heart; and an activity sensor that measures a current physical activity level of said subject.

9. A method of generating decision support information for use in a selective heart pacing, said method comprising the steps of:

detecting an intrinsic or induced atrial electric activity of a heart of a subject;

measuring an intrinsic atrioventricular delay between said detected intrinsic or induced atrial electric activity and any following intrinsic ventricular electric activity;

measuring N parameters representative of N different physiological characteristics of said subject, where N≧2;

identifying, based on said measured N parameters, a sub-space of multiple sub-spaces comprises in an N-dimensional parameter space; and assigning an expected intrinsic atrioventricular delay to said identified sub-space based on said measured intrinsic atrioventricular delay, wherein said N-dimensional parameter space with assigned expected intrinsic atrioventricular delays constitutes said decision support information wherein said assigning comprises determining a time-weighted average of said measured intrinsic atrioventricular delay and at least one previously measured intrinsic atrioventricular delay assigned to said identified sub-space and assigning said time-weighted average to said identified sub-space.

10. The method according to claim 9, wherein said parameter measuring step comprises the steps of:

measuring a current heart rate of said heart; and measuring a current physical activity level of said subject.

11. A method of selectively pacing a heart of a subject, said method comprising the steps of:

measuring N parameters representative of N different physiological characteristics of said subject, where N≧2;

identifying, based on said measured N parameters, a sub-space of an N-dimensional parameter space comprising multiple sub-spaces, where at least a portion of said multiple sub-spaces has a respective assigned expected intrinsic atrioventricular delay;

providing an expected intrinsic atrioventricular delay associated with said identified sub-space;

estimating an a priori probability that a detected intrinsic or induced atrial electric activity of said heart will trigger intrinsic ventricular electric activity within a target atrioventricular delay based on said expected intrinsic atrioventricular delay; and selectively pacing said heart based on said estimated a priori probability.

12. The method according to claim 11, wherein said providing step comprises the steps of:

locating, if said identified sub-space has not any assigned intrinsic atrioventricular delay, a sub-space having an assigned intrinsic atrioventricular delay and minimizing an Euclidian distance in said N-dimensional parameter space to said identified sub-space; and providing said intrinsic atrioventricular delay of said located sub-space.

13. The method according to claim 11, wherein said estimating step comprises estimating said a priori probability based on a comparison of said expected intrinsic atrioventricular delay and a threshold delay.

14. The method according to claim 11, wherein said selectively pacing step comprises the steps of:

applying a pacing pulse to said heart if said a priori probability indicates a low probability of triggering ventricular contraction; and awaiting an expected intrinsic triggering of ventricular contraction without any application of said pacing pulse to said heart if said a priori probability indicates a high probability of triggering ventricular contraction.

15. The method according to claim 11, further comprising measuring a delay between a detected intrinsic or induced atrial electrical activity of said heart and any following intrinsic ventricular contraction if said a priori probability indicates a high probability of triggering ventricular contraction.

16. The method according to claim 15, wherein said parameter measuring step comprises the steps of:

measuring a current heart rate of said heart; and measuring a current physical activity level of said subject.

* * * * *